United States Patent
Bergsma et al.

(10) Patent No.: US 7,344,741 B2
(45) Date of Patent: Mar. 18, 2008

(54) FOOD ADDITIVE

(75) Inventors: Jacob Bergsma, Haren (NL); Anja Neubauer, Groningen (NL); Franciscus Johannes Gerardus Boerboom, Zeist (NL)

(73) Assignee: Cooperatie Avebe U.A., Veendam (NL)

( * ) Notice: Subject to any disclaimer, the term of this patent is extended or adjusted under 35 U.S.C. 154(b) by 0 days.

(21) Appl. No.: 10/515,761

(22) PCT Filed: May 27, 2003

(86) PCT No.: PCT/NL03/00394

§ 371 (c)(1),
(2), (4) Date: May 25, 2005

(87) PCT Pub. No.: WO03/099038

PCT Pub. Date: Dec. 4, 2003

(65) Prior Publication Data

US 2005/0249867 A1 Nov. 10, 2005

(30) Foreign Application Priority Data

May 28, 2002 (EP) .................................. 02077098

(51) Int. Cl.
*A23L 1/0522* (2006.01)
(52) U.S. Cl. ........................................ 426/28; 426/661
(58) Field of Classification Search ...................... None
See application file for complete search history.

(56) References Cited

U.S. PATENT DOCUMENTS

| | | | |
|---|---|---|---|
| 4,603,110 A | 7/1986 | Morehouse et al. | |
| 5,322,778 A * | 6/1994 | Antrim et al. | 435/99 |
| 5,651,828 A | 7/1997 | Whistler | |
| 6,136,571 A * | 10/2000 | Liaw et al. | 435/96 |
| 6,303,346 B1 * | 10/2001 | Liaw et al. | 435/96 |
| 2002/0164723 A1 * | 11/2002 | Liaw et al. | 435/96 |
| 2003/0134395 A1 * | 7/2003 | Shetty et al. | 435/96 |
| 2003/0134396 A1 * | 7/2003 | Shetty et al. | 435/99 |
| 2005/0260719 A1 * | 11/2005 | Liaw et al. | 435/105 |

FOREIGN PATENT DOCUMENTS

| | | |
|---|---|---|
| EP | 0 149 258 A | 7/1985 |
| EP | 0 486 936 A | 5/1992 |
| EP | 0 616 778 A | 9/1994 |
| EP | 0 846 704 A | 6/1998 |
| WO | WO 01/21011 A | 3/2001 |

OTHER PUBLICATIONS

Atkins et al., "The Influence of Pullulanase and α-Amylase upon the Oligosaccharide Product Spectra of Wheat Starch Hydrolysates", *Starch/Stärke*, 37(4):126-131(1985).

* cited by examiner

*Primary Examiner*—Carolyn Paden
(74) *Attorney, Agent, or Firm*—Hoffmann & Baron, LLP

(57) ABSTRACT

The invention relates to a food additive, in particular for food products such as dressings, mayonnaises, spreads or other food products having a reduced fat content. The invention further relates to a process for preparing the food additive and to its use in the preparation of food products. It has been found that a method according to the present invention allows the preparation of a food additive suitable for use as a whitener and/or a fat/protein substitute, depending on the manner in which the method is carried out.

15 Claims, 1 Drawing Sheet

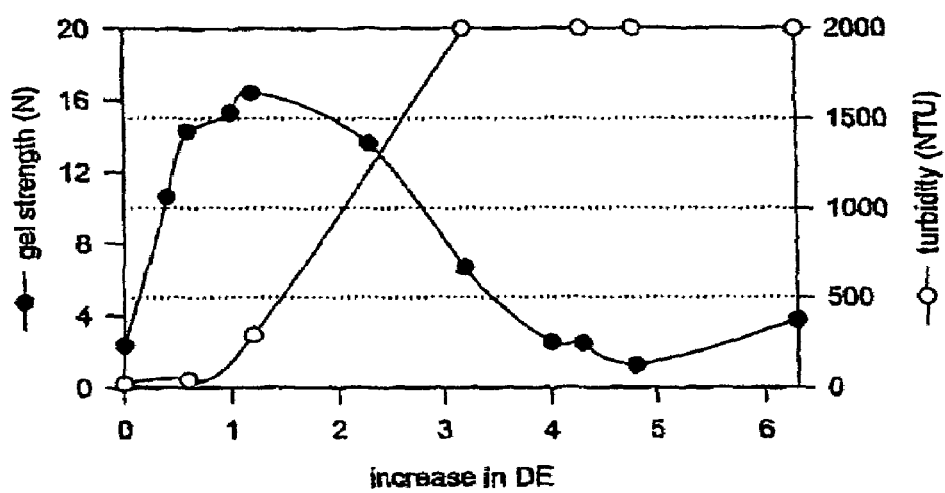
*Figure 1: Turbidity and gel strength of debranched Paselli SA2's*

FOOD ADDITIVE

This application is the U.S. National Phase of International Application Number PCT/NL03/00394 filed on 27 May 2003, which claims priority to European Application Number EP02077098.8 filed on May 28, 2002, both of which are incorporated herein by reference.

BACKGROUND OF THE INVENTION

The invention relates to a food additive, in particular for food products such as dressings, mayonnaises, spreads and other products hang a reduced fat content. The invention further relates to a process for preparing the food additive and to its use in the preparation of food products.

The use of modified starch as a food additive is for example known from EP 0 149 258, which relates to the use of hydrolyzed starch as partial fat- and/or oil-replacement in foodstuff.

EP 0 486 936 describes the use of a enzymatically debranched starch as a replacement for fat.

EP 0 372 184 relates to enzymatically debranched starch which is capable of forming a thermally reversible gel, a high strength gel, a stable, opaque cloud, or a lubricating, fat-like texture in an aqueous dispersion. It is shown in Examples 6 and 10 of EP 0 372 184 that no stable opaque product is obtained if an hydrolyzed starch is debranched.

A disadvantage of preparing modified starches by way of debranching only is that it is very difficult, if not impossible, to carry out such a preparation in an economic attractive manner (i.e. at high solids content), while still obtaining a product having the desired qualities. At high solids contests, the modification reaction leads to a product which has unfavorable handling properties.

EP 0 846 704 discloses a highly fermentable resistant starch which is obtained by thinning a starch and enzymatically debranching the thinned starch, wherein retrogradation occurs during debranching. It is unclear to what degree that debranching is carried out.

It is an object of the present invention to provide a method for providing a food additive based upon a starch. It has been found that it is possible to prepare a food additive with particular properties by hydrolyzing and debranching a starch in a particular way. It has been found that a method according to the present invention allows the preparation of a food additive suitable for use as a whitener and/or a fat/protein substitute, depending on the manner in which the method is carried out.

SUMMARY OF THE INVENTION

In a first aspect, the present invention relates to a method for preparing a food additive comprising the steps of hydrolysing and debranching a starch, wherein the step of debranching is initiated during or after the step of hydrolysis.

The present invention further relates to a food additive obtainable by a method according to any of the preceding claims comprising a hydrolyzed and debranched starch and to the use of said food additive to impart particular desired properties to a food product.

A food additive according to the invention has been found to provide creaminess, body, texture and fatty mouth-feel, thus making it an attractive fat and/or protein substitute. Advantages of using a food additive according to the invention as a replacement for fat and/or protein in a food product include advantages in price-performance, caloric value and/or less off-taste as lower dosages suffice to achieve the same effect on a food product wherein the food additive is incorporated.

A food additive according to the invention has further been found suitable for use as a spray drying aid, e.g. for flavor encapsulation, as a coating aid or as a gelling enhancer.

It has further been found that a food additive obtainable via a method according to the invention has a remarkable gelling potential (high gelling rate, high gel strength, and little or no after-gelling) taking into account its Dextrose-Equivalent value (DE).

A food additive according to the present invention may offer a beneficial effect of acting as a whitener, a gelling agent, or a combination thereof.

A food additive according to the invention has been found to have a lower solubility, a higher gel strength in comparison to a starch which is modified by hydrolysis only. Further it has been found that the rate of gel-formation is generally high and the sensitivity of the gel strength to temperature is relatively low (in particular between 0 and 30° C.).

A food additive according to the invention can very suitably be used in the preparation of a food product, in a cold or a warm application. Accordingly the present invention also relates to the use of an additive in the preparation of a food product and to a food product containing a food additive according to the invention.

Preferred examples of food products, wherein a food additive according to the invention can be used include food products chosen from the group of spreads, margarines, dressings, puddings, custard, low fat cheeses, toppings, sauces, mayonnaises, ice creams, yogurts, frozen desserts, icings, sour creams, batters, batter coatings, baked products, bakery creams, creamers, shortenings, and baby foods.

DETAILED DESCRIPTION OF THE INVENTION

Examples of suitable starches as a raw material include maize, wheat, barley, rice, triticale, millet, tapioca, arrow root, banana, potato, sweet potato, high amylose type starches, such as from amylomaize, wrinkled peas, or mung beans. Preferably, the starch is an amylose containing starch derived from corn, wheat, potato, tapioca, or sweet potato starches. Very good results have been achieved with potato starch.

The starch is preferably a native starch. As used in the context of the present invention, the term 'native starch' is intended to refer to starch that is isolated from its natural source product, but which in principle has undergone substantially no physical or chemical modification. In fact, this term is commonly used in the art to refer to such starch products. A possibility for a starch derivative that could be used to prepare a food additive according to the invention is an octenyl succinylated starch.

It has been found that by controlling the extent to which the hydrolyzing and/or the debranching contribute to the DE is such that their respective contribution to the increase in tile dextrose equivalent value ($\Delta$DE) during the method is within a particular range, product qualities can be modified. Thus the obtained product may for example have particularly advantageous properties as a whitener, as a fat substitute or both.

Suitable hydrolysis procedures are known in the art, e.g. from "Modified Starches: Properties and Uses", O. B. Wurzburg, CRC Press Inc., 1987". Hydrolysis can for example be performed by mild acid degradation (see also Shildneck, Smith (1967). Production and uses of acid-modified starch, in: Starch chemistry and technology, Volume II: Industrial aspects, editors Whistler & Paschall, Academic Press, 217-235), enzymatic treatment (maltodextrinization) or using dry heat (pyrodextrinization, see also Evans, Wurzburg (1967). Production and use of starch dextrins, in: Starch chemistry and technology, Volume II: Index aspects, editors Whistler & Paschall, Academic Press, 254-278).

Suitable acids that can be used in mild acid degradation include both Brønsted and Lewis acids. Particularly suitable are mineral acids, such as hydrochloric acid, sulfuric acid, nitric acid, phosphoric acid and combinations thereof. The amount in which the acid is added to the starch depends on the desired degree of hydrolysis and the reaction time available. When phosphoric acid is used, it is also possible to use partially neutralized phosphoric acid. Under the preferred reactions conditions, the pH is lower than 7, more preferably in the range of 4 to 6. Optionally, the hydrolyzed product may be neutralized by mixing with alkaline salts, such as sodium carbonate, to terminate hydrolysis.

Preferably the starch is hydrolyzed enzymatically. A typical process comprises jet-cooking the starch, adding enzyme during or after jet-cooking and terminating the reaction by jet-cooking the converted starch, which may be recovered by spray-drying. The chosen conditions can readily determined by the skilled professional. Very good results have been achieved with an enzymatic hydrolysis using an α-amylase.

Preferably the step of hydrolysis is performed to achieve a dextrose equivalent (DE) of between 0.5 and 7, more preferably between 1.5 and 4. The DE as used herein is the value as measured by using the Luff-Schoorl method (Schoorl (1929), Suiker titratie, Chemisch weekblad, 5, p. 130).

It has been found to be advantageous to start the hydrolysis of the starch prior to the debranching. It is possible that the hydrolysis is carried out completely until the desired degree of hydrolysis is obtained, defined by the DE of the starch. It is also possible that the hydrolysis and the debranching are carried out simultaneously or partially simultaneously. However, in accordance with the invention, the hydrolysis is started prior to the moment at which debranching is started.

Debranching may be performed in any way. Preferably debranching is carried out enzymatically. An enzymatic debranching treatment will generally lead to formation of short chain amylose. Debranching enzymes are roughly divisible into two categories: pullulanases and isoamylases. The first category is, by the International Union of Biochemistry (1984), officially referred to as E.C. 3.2.1.41 α-dextrin endo-1,6-glucosidase. By definition, enzymes of this category are capable of hydrolyzing 1,6-α-D-glucosidic bonds in pullulan, glycogen and in the α- and β-limits dextrins of amylopectin and glycogen. The second category falls with the class of E.C. 3.2.1.68. Enzymes of this category are capable of hydrolyzing 1,6-α-D-glucosidic bonds in glycogen, amylopectin and their respective β-limit dextrins. In general, isoamylases are well suited for debranching longer chains in the starch. In view of commercial availability it is preferred that a pullulanases is used for debranching the starch. Examples of particularly suitable pullulanases are the commercially available products known by their trade names Optimax L300 (Genencor), Optimax L1000 (Genencor) and Promozyme 200L (Novo Enzymes).

Optimum dosages of enzyme and optimum conditions for the enzymatic treatment, are governed by the level of enzyme activity which is dependent on the source and supplier of the enzyme, and the concentration of the enzyme in commercially available batches. Although a process according to the invention preferably employs an enzyme in dissolved state, it is equally possible to use an enzyme immobilized on a solid support.

The debranching is continued until the desired degree of conversion is achieved. The process can be terminated by changing the conditions, e.g. temperature or pH, outside of the optimum range for the specific enzyme used. The degree of the conversion can suitably be determined by measurement of the reducing groups that are formed as a result of debranching. This can be done e.g. by measurement of the reducing power as dextrose equivalent (DE) according to commonly used methods like Luff-Schoorl.

For example, good results have been achieved with a method wherein the debranching is terminated at an increase in DE due to debranching of 0.2-4. The obtained food additive has inter alia been found to be particularly suitable for use in solid food emulsions such as spreads, margarines and low fat cheeses, in spoonable products such as toppings, cold sauces, mayounnaises, dressings, puddings and custards, in emulsified meat products, in liquid foods and baby foods, in powdered and liquid soups and sauces, in ice cream, frozen desserts and icings, in batter coatings and breadings. Such a method has also been found to be particularly suitable for preparing an additive suitable as a protein or fat replacer, preferably in yogurts, low-fat sour creams and sauces, as a spray drying aid for flavor encapsulation, as partial fat substitutes, preferably in shortenings and creamers or as gelling enhancer (in particular to improve the gelling of starches).

Also good results have been obtained with a method wherein the debranching is terminated at an increase in DE due to debranching of >1, preferably between 1 and 7. The obtained food additive has inter alia been found to be particularly suitable for use in solid food emulsions such as spreads, margarines and low fat cheeses, in spoonable products such as toppings, cold sauces, mayonnaises, dressings, puddings and custards, in yogurts, low-fat sour creams and sauces, in batter coatings and breadings, as coating aids or in shortenings and creamers. Such a method has also been found to be particularly suitable for preparing an additive suitable as a spray drying aid for flavor encapsulations, as a coating aid, as gelling enhancer (in particular to improve the gelling of starches), or as whitener.

Once the debranching has reached its desired extent of completion, the starch product may be dried in any suitable mater, e.g. by spray-drying. If desired, the product may be chemically or physically modified in any known manner.

The invention will now be further elucidated by the following, non-restrictive examples.

EXAMPLE 1

Materials and Methods
Reaction Conditions
800 l of a 30% (w/w) solution of Paselli SA2 (AVEBE, Veendam, The Netherlands) with a DE of 2.4 (measured by the Luff-Schoorl method) were incubated under stirring at 60° C. The pH was adjusted to 4.4 using 1 M $H_2SO_4$. After addition of 0.3% (w/w on dry substance) Optimax L1000 (Genencor) the debranching reaction proceeded for 16 hours. The reaction was stopped by increasing the pH to 7 with 10% NaOH and subsequently the enzyme was inactivated by heating the mixture to 90° C. for 30 minutes. 120 kg product with a DE of 6.5 were obtained after spray-drying.

Analytical Methods

Dextrose Equivalent (DE in %)

Dextrose equivalent was measured using the Luff-Schoorl method (Schoorl (1929), Suiker titratie, Chemisch weekblad, 5, p. 130).

Preparation of Gels

20% (w/w) gels were prepared by adding 40 g (dry substance) of the products to 160 ml tap water (10-12° DH). The mixture was heated in a steal pan (16 cm diameter) under intensive mixing with a whisk and cooked for at least 1 minute. The weight was adjusted to 200 ml (correction for evaporated water) and the mixture was filled into a 200 ml beaker (high type).

Texture Analyzer Measurements

Gel strength was measured using a the analyzer (Stable micro systems TA-HDi) using the backwards-extrusion technique. A probe of 1 inch was pressed 40 mm into the gel and removed again. The following settings were applied:

Pn test speed 5 mm/s
test speed 2 mm/s
post test speed 5 mm/s
distance 40.0 mm
trigger auto, 8 gram Products were compared on the basis of the maximum forces.

Turbidity

For turbidity measurements the samples were dissolved in a 1% NaCl solution in demineralized water at a concentration of 2% (w/w dry substance) in a rapid visco analyzer (RVA-4, Newport Scientific). The following profile was used (amount of mixture: 40 g):

start temperature 50° C.
10 s stirring at 500 rpm
50 s stirring at 250 rpm
in 222 s heating from 50° C. to 95° C.
600 s at 95° C.

The mixture was transferred in a cuvette and measured in a RATIO/XR turbidimeter (HACH) after standing 1 h at room temperature.

Results

Table 1 and FIG. 1 show values of debranched Paselli SA2 (at different DE's) with regard to whiteness, and gel strength. gives the values measured. High gel strengths are obtained at a ΔDE of 0.5-2.5, low gel strengths from ΔDE>4. Whiteness increases with increasing degree of debranching. At a ΔDE of 3.2 or more the maximum measurable value (2000 NTU) is exceeded.

TABLE 1

Turbidity and gel strength of debranched Paselli SA2's

| increase in DE | gel strength (N) | turbidity (NTU) |
|---|---|---|
| 6.3 | 3.79 | >2000 |
| 4.8 | 1.28 | >2000 |
| 4.3 | 2.48 | >2000 |
| 4.0 | 2.52 | |
| 3.2 | 6.68 | >2000 |
| 2.3 | 13.64 | |
| 1.2 | 16.45 | 292 |
| 1.0 | 15.34 | |
| 0.6 | 14.31 | 43.8 |

TABLE 1-continued

Turbidity and gel strength of debranched Paselli SA2's

| increase in DE | gel strength (N) | turbidity (NTU) |
|---|---|---|
| 0.4 | 10.62 | |
| 0.0 | 2.38 | 20.8 |

EXAMPLE 2

Gels were prepared from Perfectamyl Gel MB (AVEBE, Veendam, The Netherlands) or combinations with the product prepared in Example 1. All percentages given refer to the dry solids of the individual components (Perfectamyl GelMB: 15.0% moisture, Product Example 1: 9.9% moisture).

Samples up to 1-kg final weight were dispersed in an open pan using a whisk. The required amounts of the powders were weighed into the pan and the weight was adjusted to 1 kg with tap water. While stirring the content of the pan was heated to boiling. Boiling was continued for 1 min. at moderate heat. The evaporated water was compensated for by adding hot water.

The content was poured into three beakers (250 ml high-model) which were covered with watch glasses. These beakers were incubated in a water bath at 20° C. for the times indicated.

Gels were analysed with a Brookfield DV-1+ Viscometer in helipath configuration (10 r.p.m.). The helipath spindles used were dependent on the gel strengths. The types are indicated in the experimental section. Al gel-strengths were measured at 20° C. The results are shown in Table 2.

TABLE 2

Gel strengths gels at 7.5 and 9.0% dry solids.

| | Composition of dry solids in gel (% by weight on total gel) | | |
|---|---|---|---|
| Time of gelling (hrs) | Perfectamyl Gel MB (7.5%) | Perfectamyl Gel MB (7.5%) Product Example 1 (1.5%) Gel strength (mPa · s) | Perfectamyl Gel MB (9%) |
| 25 | 7360 (A) | 27300 (A) | 20100 (A) |
| 48 | 11700 (A) | 48000 (C) | 34000 (A) |
| 120 | 20800 (A) | 111000 (C) | 64000 (C) |

The invention claimed is:

1. A method for preparing a food additive comprising hydrolyzing and debranching a starch, wherein the hydrolyzing is performed enzymatically during or after jet-cooking the starch to achieve a dextrose equivalent of between 0.5 and 7.0, wherein the hydrolyzing enzyme utilized is an alpha-amylase, wherein the step of debranching is initiated during or after hydrolyzing the starch and terminated at an increase in DE due to debranching of 0.2 to 7.0.

2. A method according to claim 1 wherein the starch is chosen from the group of corn, wheat, potato, tapioca, and sweet potato starches.

3. A method according to claim 1, wherein the starch is debranched using a pullulanase and/or isoamylase.

4. A method according to claim 1, wherein the debranching is terminated at an increase in DE due to debranching of 0.2-4.

5. A method according to claim 4, wherein the food additive is a gelling enhancer, a spray drying aid, or a protein or fat replacer.

6. A method according to claim 1, wherein the debranching is terminated at an increase in DE due to debranching of 1-7.

7. A method according to claim 6, wherein the food additive is a spray drying aid, a coating aid, a gelling enhancer, or a whitener.

8. A food additive obtainable by a method according to claim 1 comprising a hydrolyzed and debranched starch.

9. A method for preparing a food product comprising incorporating said additive according to claim 8 into food product.

10. A method according to claim 9 wherein the food product is chosen from the group of spreads, margarines, dressings, puddings, custards, low fat cheeses, toppings, sauces, mayonnaises, ice creams, yogurts, frozen desserts, icings, sour creams, bakery creams, batters, batter coatings, baked products, creamers, shortenings, baby foods, powdered soups, liquid soups and breadings.

11. Food product comprising a food additive according to claim 8.

12. Food product according to claim 11, wherein said food product is selected from the group consisting of spreads, margarines, dressings, puddings, custards, low fat cheeses, toppings, sauces, mayonnaises, ice creams, yogurts, frozen desserts, icings, sour creams, batters, bakery creams, batter coatings, baked products, creamers, shortenings, baby foods, powdered soups, liquid soups and breadings.

13. A method according to claim 1 wherein the starch is hydrolyzed to achieve a dextrose equivalent (DE) of between 1.5 and 4.

14. A method according to claim 13, wherein the debranching is terminated at an increase in DE due to debranching of 0.2-4.

15. A method according to claim 13, wherein the debranching is terminated at an increase in DE due to debranching of 1-7.

* * * * *

UNITED STATES PATENT AND TRADEMARK OFFICE
CERTIFICATE OF CORRECTION

PATENT NO. : 7,344,741 B2  Page 1 of 1
APPLICATION NO. : 10/515761
DATED : March 18, 2008
INVENTOR(S) : Bergsma et al.

It is certified that error appears in the above-identified patent and that said Letters Patent is hereby corrected as shown below:

IN THE PATENT

Column 1, line 13
Now Reads:     "products hang a reduced"
Should Read:   --products having a reduced--

Column 2, line 63
Now Reads:     "increase in "tile" dextrose"
Should Read:   --increase in the dextrose--

Column 4, line 26
Now Reads:     "mayounnaises"
Should Read:   --mayonnaises--

Column 5, line 20
Now Reads:     "measured using a the analyzer"
Should Read:   --measured using a texture analyzer--

Signed and Sealed this

Twelfth Day of August, 2008

JON W. DUDAS
*Director of the United States Patent and Trademark Office*